(12) United States Patent
Donello et al.

(10) Patent No.: US 8,211,917 B2
(45) Date of Patent: Jul. 3, 2012

(54) METHODS FOR TREATING ANXIETY

(75) Inventors: John E. Donello, Dana Point, CA (US); Lauren M. B. Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 95 days.

(21) Appl. No.: 12/669,304

(22) PCT Filed: Jul. 8, 2008

(86) PCT No.: PCT/US2008/069428
§ 371 (c)(1),
(2), (4) Date: Jan. 15, 2010

(87) PCT Pub. No.: WO2009/012082
PCT Pub. Date: Jan. 22, 2009

(65) Prior Publication Data
US 2010/0197730 A1    Aug. 5, 2010

Related U.S. Application Data

(60) Provisional application No. 60/950,144, filed on Jul. 17, 2007.

(51) Int. Cl.
*A01N 43/40* (2006.01)
*A01N 43/36* (2006.01)
(52) U.S. Cl. .................. 514/336; 514/422
(58) Field of Classification Search .............. None
See application file for complete search history.

(56) References Cited

U.S. PATENT DOCUMENTS

| 2010/0048642 A1* | 2/2010 | Donello et al. ............. 514/343 |
| 2010/0093793 A1* | 4/2010 | Donello et al. ............. 514/314 |
| 2010/0190792 A1* | 7/2010 | Donello et al. ............. 514/237.8 |

FOREIGN PATENT DOCUMENTS

| WO | WO 03/045928 | 6/2003 |
| WO | WO 2006/081252 | 8/2006 |
| WO | WO 2006/081273 | 8/2006 |
| WO | WO 2008/109287 | 9/2008 |
| WO | WO 2008/109610 | 9/2008 |
| WO | WO 2008109286 A1 * | 9/2008 |

OTHER PUBLICATIONS

Ohaeri, "The Management of Anxiety and Depressive Disorders", International Journal of Mental Health and Addiction, vol. 4, No. 2, pp. 103-118, 2006.
Wolf et al, "The use of the elevated plus maze as an assay of anxiety-related behavior in rodents", vol. 2, No. 2, pp. 322-328, 2007.

* cited by examiner

*Primary Examiner* — Sreeni Padmanabhan
*Assistant Examiner* — Svetlana M Ivanova
(74) *Attorney, Agent, or Firm* — Joel B. German; Krishna G. Banerjee

(57) ABSTRACT

Disclosed are methods of treating anxiety by administering to a patient in need of such treatment a compound having the following formula (I).

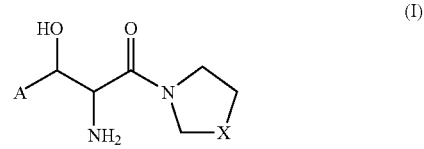

14 Claims, No Drawings

METHODS FOR TREATING ANXIETY

CROSS-REFERENCE

This application is a 371 of PCT /US08/069428 filed July 8, 2008 which claims the benefit of U.S. application Ser. No. 60/950,144 filed July 17, 2007, which is hereby incorporated by reference in its entirety.

Disclosed herein is a method of treating anxiety by administering to a patient in need of such treatment a compound having the following formula:

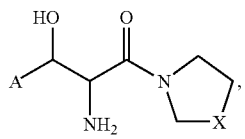

wherein X is $CH_2$ or $CH_2$—$CH_2$,
A is aryl or heteroaryl having 0, 1, 2, or 3 atoms selected from the group consisting of N, S, and O,
wherein A has 0, 1, 2, or 3 substituents independently selected from the group consisting of 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms,

DETAILED DESCRIPTION OF THE INVENTION

Anxiety

"Anxiety" refers to an emotional state of apprehension or other unease that is distressing or otherwise unpleasant to a person. It is the central feature of various anxiety disorders, including, for example, generalized anxiety disorder, obsessive-compulsive disorder, panic disorder, phobic disorders, and stress disorders. Anxiety may also occur comorbidly with other mental disorders, such as with mixed-anxiety depression, or may be a symptom of them, such as in premenstrual dysphoric syndrome. Anxiety may also occur comorbidly with conditions other than mental disorders, such as with Alzheimer's disease or fibromyalgia, for example.

General anxiety disorder is characterized by excessive anxiety, often with little provocation. The anxiety often has more than one object (for example, finances and health) and changes over time. It is often accompanied by one or more physical symptoms, such as fatigue, headaches, muscle tension, muscle aches, difficulty swallowing, trembling, twitching, irritability, sweating, hot flashes, restlessness, and difficulty concentrating.

Obsessive-compulsive disorder is characterized by intrusive ideas (such as a fear of contamination, fear of flying) or impulses (such as inflicting harm on others) or a compulsion to perform certain behaviors in order to lessen the anxiety provoked by such ideas of impulses. The compulsions often involve repetitive behavior, such as repeatedly washing hands, counting, or uttering a certain phrase, and may or may not be observable to others.

A panic attack is characterized by an intense, often spontaneous episode of anxiety accompanied by one or more cognitive or somatic symptoms. Cognitive symptoms include a fear of dying, fear of going crazy or losing control, feelings of unreality, strangeness, or detachment from the environment. Somatic symptoms include chest pain or discomfort, dizziness, faintness, feeling of choking, flushes or chills, nausea or abdominal distress, numbness or tingling sensations, palpitations or accelerated heart rate, sensations of shortness of breath or smothering, sweating, and trembling or shaking. Panic attacks may occur spoptaneously, or may occur in connection with other anxiety disorders; a person with claustrophobia, for example, may experience a panic attack when entering an elevator. Panic disorder occurs when a person repeatedly suffers panic attacks.

Phobic disorders are characterized by intense and irrational fears of certain situations or objects, often accompanied by avoidance of the cause of the fear. There are two types: general and specific. General phobias comprise agoraphobia and social phobia. Agoraphobia is a fear of being trapped in a situation or place without escape or aid; for example, a person may fear sitting in a movie theater or riding in a bus. Social phobia is a fear provoked by certain social situations. Individuals with this phobia often fear that embarrassment or humiliation will result if they do not perform in a satisfactory way, and may fear that symptoms of anxiety—sweating, blushing, voice trembling, etc.—will become apparent, leading to further embarrassment and humiliation.

In specific phobias the source of the fear is a specific object, such as animals (zoophobia), thunderstorms (astraphobia and brontophobia), or blood (homophobia); or the source is a specific situation, such as being exposed to heights (acrophobia) or closed places (claustrophobia)

Stress disorders are generally divided into types, acute stress disorder and posttraumatic stress disorder. Acute stress disorder results from witnessing or experiencing a traumatic event; symptoms include recurring recollections of the event, increased arousal, emotional detachment, and/or amnesia, among others. Acute stress disorder is of short duration, usually four or fewer weeks. A longer duration of symptoms often indicates posttraumatic stress disorder. Posttraumatic stress disorder is characterized by recurring, frequent, unwanted recollections of a traumatic event, nightmares, feelings of depression or guilt, and emotional detachment.

The disorders described here can interfere with a person's functioning. But they need not; the compounds of the invention may be used to treat anxiety even if it is not severe. A person with occasional panic attacks, for example, may be treated with compounds of the invention even though the person may not have panic disorder; the person need not wait to suffer from repeated panic attacks or be incapacitated by them before starting treatment with the compounds of the present invention. Similarly, a patient suffering from a mild form of acute stress disorder may be treated with compounds of the invention; one need not wait for the acute disorder to progress to posttraumatic stress disorder. What matters is only that a person seeking treatment for anxiety finds the anxiety unpleasant and wishes to alleviate it and/or prevent it from occurring.

Compounds of the Invention

The method of the invention comprises administering to a patient compounds of the following formula:

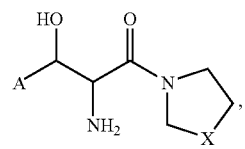

wherein X is $CH_2$ or $CH_2$—$CH_2$,
A is aryl, or is heteroaryl having 0, 1, 2, or 3 atoms selected from the group consisting of N, S, and O, wherein A has 0, 1, 2, or 3 substituents independently selected from the group consisting of 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms.

"Aryl," as used here, means any ring or ring system that contains at least one aromatic ring.

"Heteroaryl," as used here, means an aromatic ring in which 0, 1, 2, or 3 of the atoms in the ring are N, S, or O; this includes, for example, pyridinyl, thienyl, and furyl.

The substituents may be the same or different. Examples of substituents having the constraints defined here include, but are not limited to, the following:

hydrocarbyl, meaning a moiety consisting of carbon and hydrogen only, including, but not limited to,
  a. alkyl, meaning hydrocarbyl having no double or triple bonds, including, but not limited to,
    i) linear alkyl, e.g. methyl, ethyl, n-propyl, n-butyl, n-pentyl, n-hexyl, etc.,
    ii) branched alkyl, e.g. iso-propyl, t-butyl and other branched butyl isomers, branched pentyl isomers, etc.,
    iii) cycloalkyl, e.g. cyclopropyl, cyclobutyl, cyclopentyl, cyclohexyl, etc., which may optionally be fused to another cycloalkyl or phenyl substituent;
    iv) combinations of linear, branched, and/or cycloalkyl;
  b. alkenyl, e.g. hydrocarbyl having 1 or more double bonds, including linear, branched, or cycloalkenyl;
  c. alkynyl, e.g. hydrocarbyl having 1 or more triple bonds, including linear or branched (alkynyl);
  d. combinations of alkyl, alkenyl, and/or akynyl;

alkyl-CN, such as —CH$_2$—CN, —(CH$_2$)$_2$—CN; —(CH$_2$)$_3$—CN, and the like;

hydroxyalkyl, i.e., alkyl-OH, such as hydroxymethyl, hydroxyethyl, and the like;

ether substituents, including —O-alkyl, alkyl-O-alkyl, and the like;

hydroxy alkyl ether, such as —COOH, thioalkyl and thioether substituents, including —S-alkyl, alkyl-S-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl (i.e.

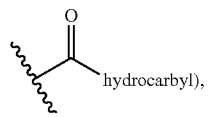

hydrocarbyl), and the like; in particular, acetyl, propionyl, and benzoyl substituents are contemplated;

phenyl and substituted phenyl; the phenyl and substituted phenyl may itself be optionally fused with another phenyl or cycloalkyl substituent;

fluorocarbons and hydrofluorocarbons such as —CF$_3$, —CH$_2$CF$_3$, etc.;

—CN; and

—F, —Cl, —Br, or —I.

Combinations of the foregoing substituents are also possible, subject to the constraints defined.

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —CO$_2$.Na$^+$ is a stable substituent consisting of 3 heavy atoms, i.e. sodium is not counted. In another example, the salt —NH(Me)$_2$$^+$C$^-$ is a stable substituent consisting of 3 heavy atoms, i.e. chlorine is not counted.

In one embodiment, A is pyridinyl, meaning that compounds of structures such as those shown below are contemplated. In these structures, R1, R2, and R3 are substituents as defined herein:

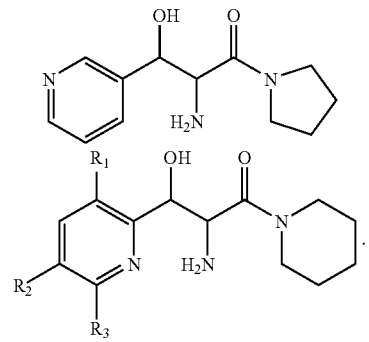

In another embodiment, A is thienyl, meaning that compounds of structures such as those shown below are contemplated. In these structures, R1 and R2 are substituents as defined herein:

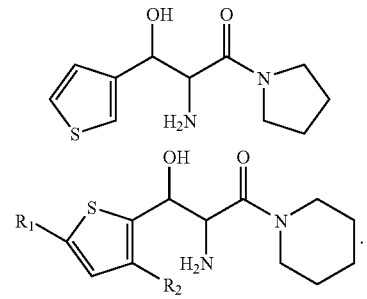

In another embodiment, A is furyl, meaning that compounds of structures such as those shown below are contemplated. In these structures, R1, R2, and R3 are substituents as defined herein:

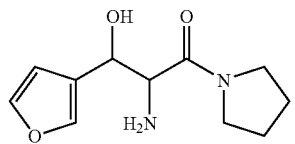

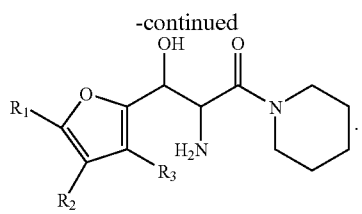

In one embodiment, each substituent is independently alkyl having from 1 to 6 carbon atoms.

In another embodiment, A is unsubstituted or has an isopropyl substituent.

In another embodiment, each substituent of B is —F, —Cl, —CH$_3$, or —CF$_3$.

In another embodiment, A is pyridyl, thienyl, furyl, pyrrolyl, pyrrolidinyl, imidazolyl, oxazolyl, thiazolyl, pyrazolyl, pyrimidinyl, quinolinyl, or pyrazinyl having 0, 1, 2, or 3 substituents.

Unless otherwise indicated, reference to a compound includes pharmaceutically acceptable salts, prodrugs, tautomers, alternate solid forms, and non-covalent complexes of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an add, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono, di and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A prodrug is a compound which is converted to a therapeutically active compound after administration. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. C1-6 alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below:

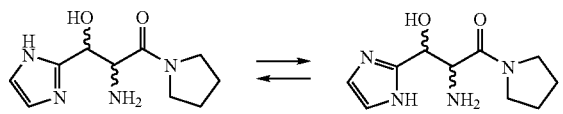

Unless stereochemistry is explicitly depicted, a structure includes every possible stereoisomer, both pure or in any possible mixture.

Alternate solid forms are different solid forms than ones that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Methods for producing the compounds of the invention are described in, for example, U.S. patent application Ser. No. 60/647,271, the disclosure of which is incorporated herein by reference.

Compositions useful in the method of the invention may further include an excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents.

Methods of Treatment

The compounds described here may be used to treat a patient suffering from anxiety.

To "treat," as used here, means to deal with medically. It includes, for example, administering a compound of the invention to prevent the onset of anxiety, to alleviate its severity, and to prevent its reoccurrence.

The compounds of the invention may be administered at pharmaceutically effective amounts. Such amounts are normally the minimum dose necessary to achieve the desired therapeutic effect; in the treatment of anxiety, this amount would be roughly that necessary to eliminate the anxiety or reduce it to tolerable levels. Such amounts are generally be effective to prevent anxiety, as well, though smaller amounts may also be used for this purpose. For human adults effective amounts generally will be in the range of 0.1-5,000 mg/day, but more preferably in the range of 1 to 3,000 mg/day, 10 mg to 500 mg/day, 500 to 1,000 mg/day, 1,000 to 1,500 mg/day, 1,500 to 2,000 mg/day, 2,000 to 2,500 mg/day, or 2,500 to 3,000 mg/day. The actual amount of the compound to be administered in any given case will be determined by a physician taking into account the relevant circumstances, such as the severity of the anxiety, the age and weight of the patient, the patient's general physical condition, and the route of administration.

The compounds are useful in the treatment of anxiety in a mammal, particularly a human being.

The patient may be given the compound orally in any acceptable form, such as a tablet, liquid, capsule, powder and the like. Other routes may be desirable or necessary, particularly if the patient suffers from nausea. Such other routes may include, for example, transdermal, intraperitonial, parenteral, subcutaneous, intranasal, intrathecal, intramuscular, intravenous and intrarectal modes of delivery.

EXAMPLES

Elevated Plus Maze Test

The elevated plus maze (EPM) exploits the instinctual anxiety response of rodents in open environments, and their subsequent tendency to avoid such environments. Testing of mice is conducted in an opaque white plastic maze that is shaped like a plus-sign. The maze is situated on a table approximately 40 inches off the floor, and is itself—40 cm high. All four arms of the maze are of equal length, at 30.5 cm each. The center portion of the maze is a 5 cm square. Two (North/South) arms of the maze have 15.25 cm high walls surrounding the entire arm except for the center portion of the "plus". The other two (East/West) arms are open, with only a 0.3 cm lip surrounding the edge, providing a visual cliff on all three exposed sides. Each arm is 5 cm wide.

EPM testing is conducted 60 minutes following intraperitoneal (i.p.) or oral gavage (p.o.) administration of the test compound. For i.p. administration, the compounds are formulated in H2O and given in a volume of 1 ml/kg body weight by injecting into the intraperitoneal cavity. For p.o. administration, the compounds are formulated in H2O and given in a volume of 1 ml/kg body weight using a 25-gauge, 1.5 inch gavage needle that is slowly inserted through the esophagus into the stomach.

Testing lasts for five minutes. The animal is placed in the center of the maze facing a closed arm and allowed to freely explore the maze for the full 5 minutes. The number of entries into the open and closed arms is counted, as is the time (in seconds) spent in the open arms. This latter variable (time in open arms) is commonly used as the primary dependent variable in this task, and is the variable presented in Table 1. Control (vehicle-treated) animals usually do not make more than 1-3 entries into the open arms, and spend between 10-20 seconds total on these arms. Anxiolytic compounds, such as diazepam or buspirone, increase the number of entries into the open arms and the time spent in the open arms. These data are also presented in Table 1, below, as positive control data.

TABLE 1

Effects of compounds of the invention in the elevated plus maze; Compounds were administered intraperitoneally except for those compounds marked with an asterisks, which were administered orally (the last vehicle dose and Compounds C, H, and I)

| COMPOUND | TREATMENT | DOSE | TIME POST DOSE (MIN) | TIME OPEN (SEC) |
|---|---|---|---|---|
| ddH$_2$O | Vehicle | 0 | 60 | 10.7 ± 5.1 |
| ddH$_2$O | Vehicle | 0 | 60 | 24.65 ± 5.7 |
| ddH$_2$O | Vehicle | 0 | 60 | 15.56 ± 3.6 |
| ddH$_2$O | Vehicle | 0 | 60 | 12.0 ± 3.0 |
| 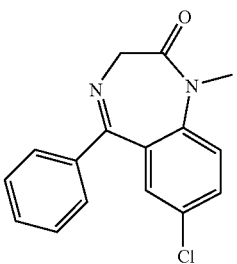 | Diazepam | 0.5 | 15 | 48.9 ± 11.3 |
|  | Diazepam | 1 | 15 | 63.0 ± 6.8 |
|  | Diazepam | 1.5 | 15 | 79.5 ± 11.0 |
|  | Diazepam | 3 | 15 | 89.6 ± 34.5 |
|  | Buspirone | 10 | 30 | 50.4 ± 5.2 |

TABLE 1-continued

Effects of compounds of the invention in the elevated plus maze;
Compounds were administered intraperitoneally except for those compounds
marked with an asterisks, which were administered orally (the last vehicle
dose and Compounds C, H, and I)

| COMPOUND | TREATMENT | DOSE | TIME POST DOSE (MIN) | TIME OPEN (SEC) |
|---|---|---|---|---|
| (structure) | Compound A | 10 | 60 | 96.41 ± 19.03 |
| (structure) | Compound B | 1 | 60 | 60.09 ± 9.17 |
| (structure) | Compound B | 10 | 60 | 39.52 ± 12.13 |
| (structure) | Compound C* | 10 | 60 | 71.2 ± 12.5 |
| (structure) | Compound D | 10 | 60 | 48.34 ± 15.6 |
| (structure) | Compound E | 10 | 60 | 47.44 ± 15.6 |
| (structure) | Compound F | 10 | 60 | 79.94 ± 18.22 |
| (structure) | Compound G | 10 | 60 | 70.97 ± 7.66 |

TABLE 1-continued

Effects of compounds of the invention in the elevated plus maze;
Compounds were administered intraperitoneally except for those compounds
marked with an asterisks, which were administered orally (the last vehicle
dose and Compounds C, H, and I)

| COMPOUND | TREATMENT | DOSE | TIME POST DOSE (MIN) | TIME OPEN (SEC) |
|---|---|---|---|---|
| 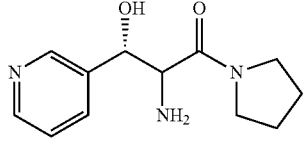 | Compound H* | 10 | 60 | 62.4 ± 7.4 |
| 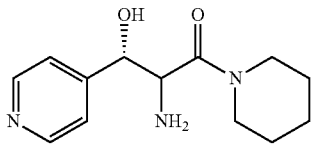 | Compound I* | 10 | 60 | 86.3 ± 9.4 |

What is claimed is:

1. A method of treating anxiety, the method comprising the step of administering to a patient in need of such treatment a compound of the formula:

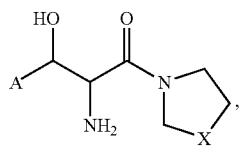

or a pharmaceutically acceptable salt thereof, wherein X is $CH_2$ or $CH_2\text{-}CH_2$, A is aryl or heteroaryl having 0, 1, 2, or 3 atoms selected from the group consisting of N, S, and O, wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

2. The method of claim 1, wherein A is selected from the group consisting of pyridinyl, thienyl, furyl, quinolinyl, methylphenyl, and biphenyl.

3. The method of claim 2, wherein A is unsubstituted.

4. The method of claim 3, wherein the anxiety is associated with generalized anxiety disorder, obsessive-compulsive disorder, panic disorder, a phobic disorder, acute stress disorder, post-traumatic stress disorder, or mixed anxiety-depression.

5. The method of claim 3, wherein the compound is:

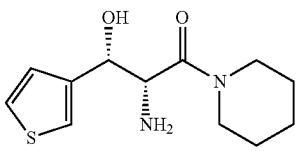

or a pharmaceutically acceptable salt thereof.

6. The method of claim 3, wherein the compound is:

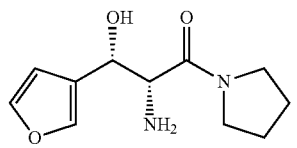

or a pharmaceutically acceptable salt thereof.

7. The method of claim 3, wherein the compound is:

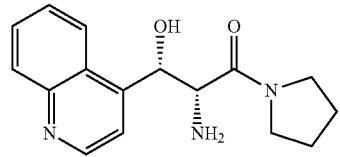

or a pharmaceutically acceptable salt thereof.

8. The method of claim 3, wherein the compound is:

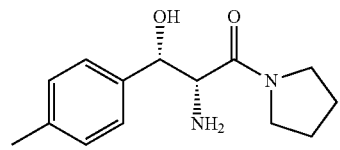

or a pharmaceutically acceptable salt thereof.

9. The method of claim 3, wherein the compound is:

or a pharmaceutically acceptable salt thereof.

10. The method of claim 3, wherein the compound is:

or a pharmaceutically acceptable salt thereof.

11. The method of claim 3, wherein the compound is:

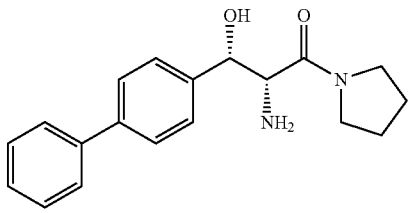

or a pharmaceutically acceptable salt thereof.

12. The method of claim 3, wherein the compound is:

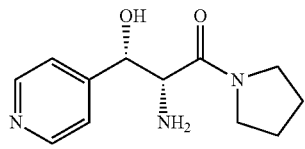

or a pharmaceutically acceptable salt thereof.

13. The method of claim 3, wherein the compound is:

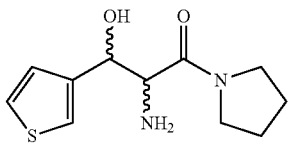

or a pharmaceutically acceptable salt thereof.

14. A method of treating anxiety, the method comprising the step of administering to a patient in need of such treatment the compound of the formula:

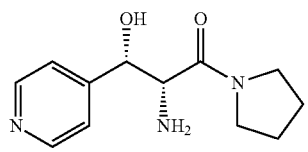

or a pharmaceutically acceptable salt thereof.

* * * * *